(12) United States Patent  (10) Patent No.: US 9,173,686 B2
Sheffer et al.  (45) Date of Patent: Nov. 3, 2015

(54) INTERSPINOUS IMPLANT

(75) Inventors: Garrett A. Sheffer, Hoboken, NJ (US);
Nathaniel E. Hawkins, Chatham, NJ (US)

(73) Assignee: EBI, LLC, Parsippany, NJ (US)

( * ) Notice: Subject to any disclaimer, the term of this patent is extended or adjusted under 35 U.S.C. 154(b) by 2294 days.

(21) Appl. No.: 11/746,204

(22) Filed: May 9, 2007

(65) Prior Publication Data

US 2008/0281423 A1  Nov. 13, 2008

(51) Int. Cl.
*A61F 2/44* (2006.01)
*A61B 17/70* (2006.01)
*A61B 19/00* (2006.01)

(52) U.S. Cl.
CPC ....... *A61B 17/7062* (2013.01); *A61B 2019/461* (2013.01)

(58) Field of Classification Search
CPC ................. A61B 17/7062; A61F 2002/30135; A61F 2002/6685; A61F 2002/443; A61F 2/44
USPC .............. 248/219.4; 623/17.11, 17.13, 17.16; 606/248, 249, 286, 900–902, 70, 71, 606/151
See application file for complete search history.

(56) References Cited

U.S. PATENT DOCUMENTS

| | | | |
|---|---|---|---|
| 5,314,477 A * | 5/1994 | Marnay | 623/17.15 |
| 5,645,599 A | 7/1997 | Samani et al. | |
| 5,683,464 A | 11/1997 | Wagner et al. | |
| 6,139,579 A | 10/2000 | Steffee et al. | |
| 6,238,397 B1 | 5/2001 | Zucherman et al. | |
| 6,293,949 B1 | 9/2001 | Justis et al. | |
| 6,419,676 B1 | 7/2002 | Zucherman et al. | |
| 6,440,169 B1 | 8/2002 | Elberg et al. | |
| 6,626,943 B2 | 9/2003 | Eberlein et al. | |
| 6,743,257 B2 | 6/2004 | Castro | |
| 6,761,719 B2 | 7/2004 | Justis et al. | |
| 7,011,685 B2 | 3/2006 | Arnin et al. | |
| 7,108,697 B2 * | 9/2006 | Mingozzi et al. | 606/286 |
| 7,497,859 B2 | 3/2009 | Zucherman et al. | |
| 2004/0106995 A1 | 6/2004 | Le Couedic et al. | |
| 2005/0125063 A1 | 6/2005 | Matge et al. | |
| 2005/0131412 A1 * | 6/2005 | Olevsky et al. | 606/69 |
| 2005/0203624 A1 | 9/2005 | Serhan et al. | |
| 2005/0261768 A1 | 11/2005 | Trieu | |
| 2005/0273100 A1 * | 12/2005 | Taylor | 606/61 |
| 2006/0015181 A1 | 1/2006 | Elberg | |
| 2006/0084988 A1 | 4/2006 | Kim | |
| 2006/0085070 A1 | 4/2006 | Kim | |

(Continued)

FOREIGN PATENT DOCUMENTS

EP  743045 A2 * 11/1996  ............... A61F 2/44
EP  1330987 A1  7/2003

(Continued)

OTHER PUBLICATIONS

Partial European Search Report (R.64 EPC) mailed Aug. 25, 2008 for European Patent Application No. EP 08251646.

*Primary Examiner* — Brian Pellegrino
(74) *Attorney, Agent, or Firm* — Schwegman Lundberg & Woessner, P.A.

(57) ABSTRACT

An interspinous implant. The interspinous implant includes a resilient S-shaped body having first and second saddle-shaped portions. First and second stirrup-shaped brackets extend in opposite directions from the first and second saddle-shaped portions for engaging first and second spinous processes.

18 Claims, 15 Drawing Sheets

(56) References Cited

U.S. PATENT DOCUMENTS

| | | |
|---|---|---|
| 2006/0149278 A1 | 7/2006 | Abdou |
| 2006/0184171 A1 | 8/2006 | Biedermann et al. |
| 2006/0271049 A1 | 11/2006 | Zucherman et al. |
| 2007/0032790 A1 | 2/2007 | Aschmann et al. |
| 2007/0106298 A1 | 5/2007 | Carli et al. |
| 2007/0161992 A1 | 7/2007 | Kwak et al. |
| 2007/0161993 A1 | 7/2007 | Lowery et al. |
| 2007/0162000 A1 | 7/2007 | Perkins |
| 2007/0162001 A1 | 7/2007 | Chin et al. |
| 2007/0162002 A1 | 7/2007 | Tornier |
| 2007/0162003 A1 | 7/2007 | Tornier et al. |
| 2007/0162004 A1 | 7/2007 | Tornier et al. |
| 2007/0162005 A1 | 7/2007 | Peterson et al. |
| 2007/0191837 A1* | 8/2007 | Trieu ............... 606/61 |
| 2007/0225706 A1 | 9/2007 | Clark et al. |
| 2007/0233076 A1 | 10/2007 | Trieu |
| 2007/0260245 A1 | 11/2007 | Malandain et al. |
| 2007/0265623 A1 | 11/2007 | Malandain et al. |
| 2007/0276373 A1 | 11/2007 | Malandain |
| 2007/0282340 A1 | 12/2007 | Malandain |
| 2008/0147192 A1 | 6/2008 | Edidin et al. |
| 2008/0161818 A1 | 7/2008 | Kloss et al. |
| 2008/0255668 A1 | 10/2008 | Fallin et al. |
| 2008/0262622 A1 | 10/2008 | Butler |
| 2008/0281423 A1 | 11/2008 | Sheffer et al. |
| 2008/0294200 A1 | 11/2008 | Kohm et al. |
| 2009/0012528 A1 | 1/2009 | Aschmann et al. |
| 2009/0054988 A1 | 2/2009 | Hess |
| 2009/0054989 A1 | 2/2009 | Baumgartner et al. |
| 2009/0234389 A1 | 9/2009 | Chuang et al. |
| 2009/0254122 A1 | 10/2009 | Khalife |
| 2009/0264927 A1 | 10/2009 | Ginsberg et al. |
| 2009/0265006 A1 | 10/2009 | Seifert et al. |
| 2009/0270919 A1 | 10/2009 | Dos Reis, Jr. |

FOREIGN PATENT DOCUMENTS

| | | |
|---|---|---|
| EP | 1945117 A2 | 7/2008 |
| EP | 1994901 A1 | 11/2008 |
| WO | WO-2006110578 | 10/2006 |
| WO | WO-2007134113 | 11/2007 |
| WO | WO-2008136877 A1 | 11/2008 |

* cited by examiner

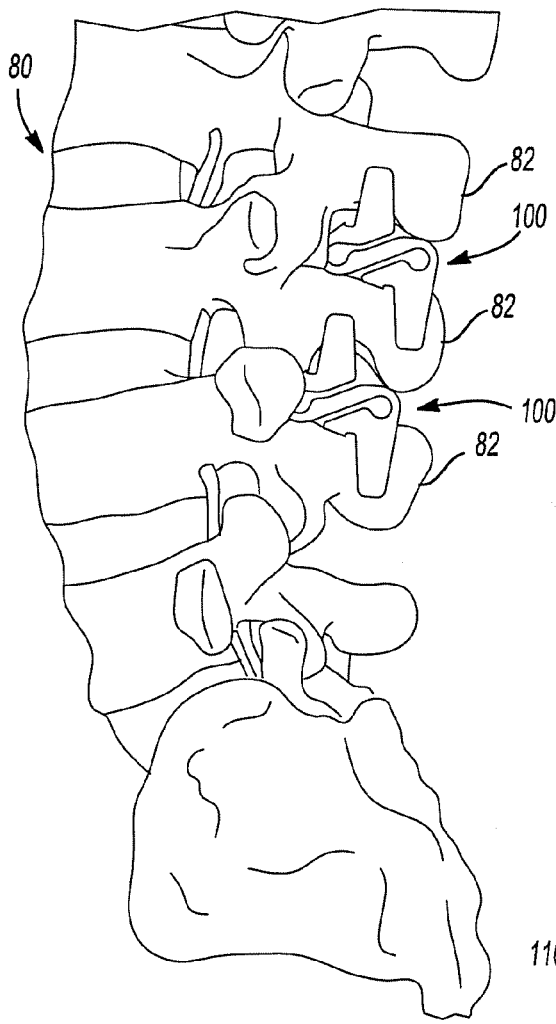
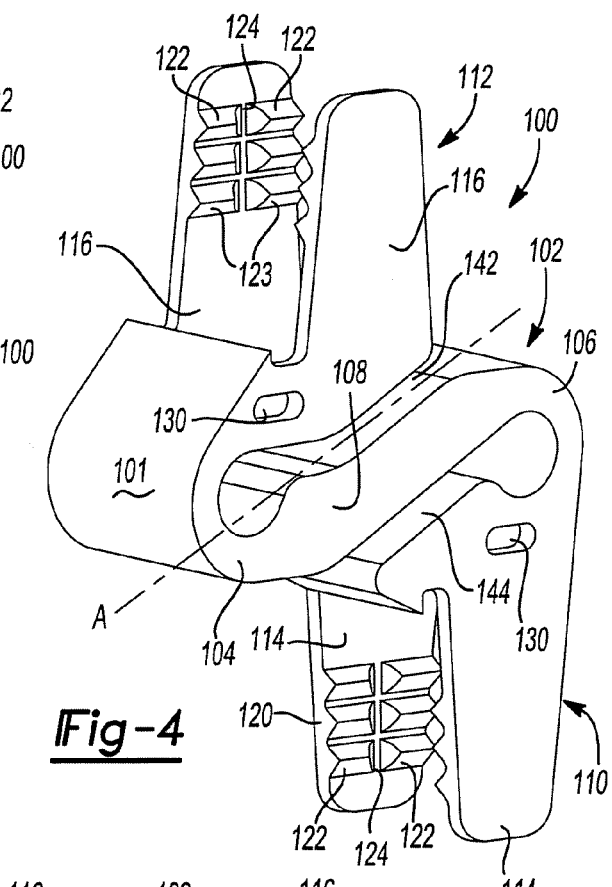
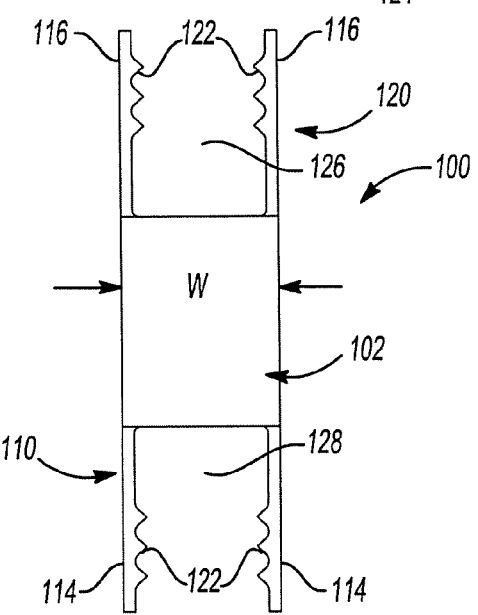
Fig-3
Fig-4
Fig-5

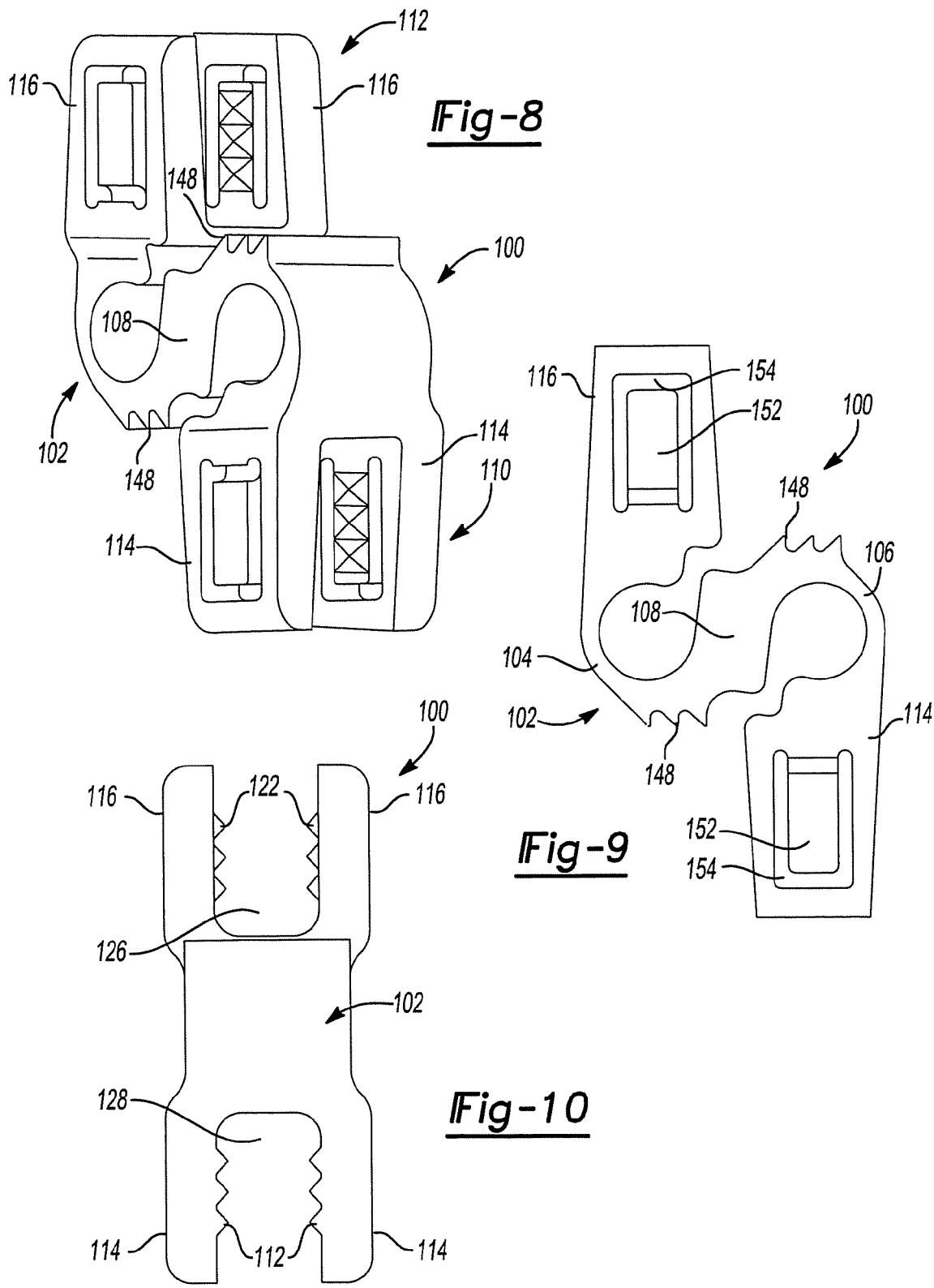

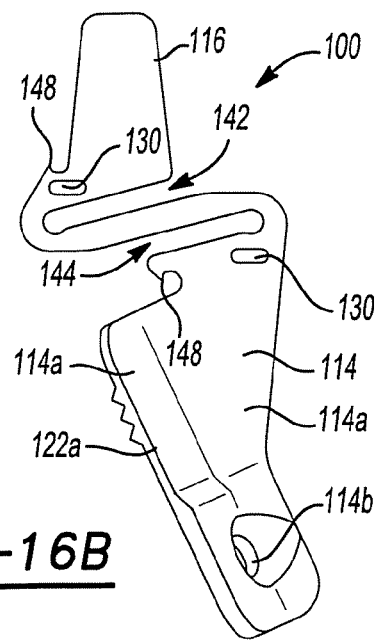
Fig-16
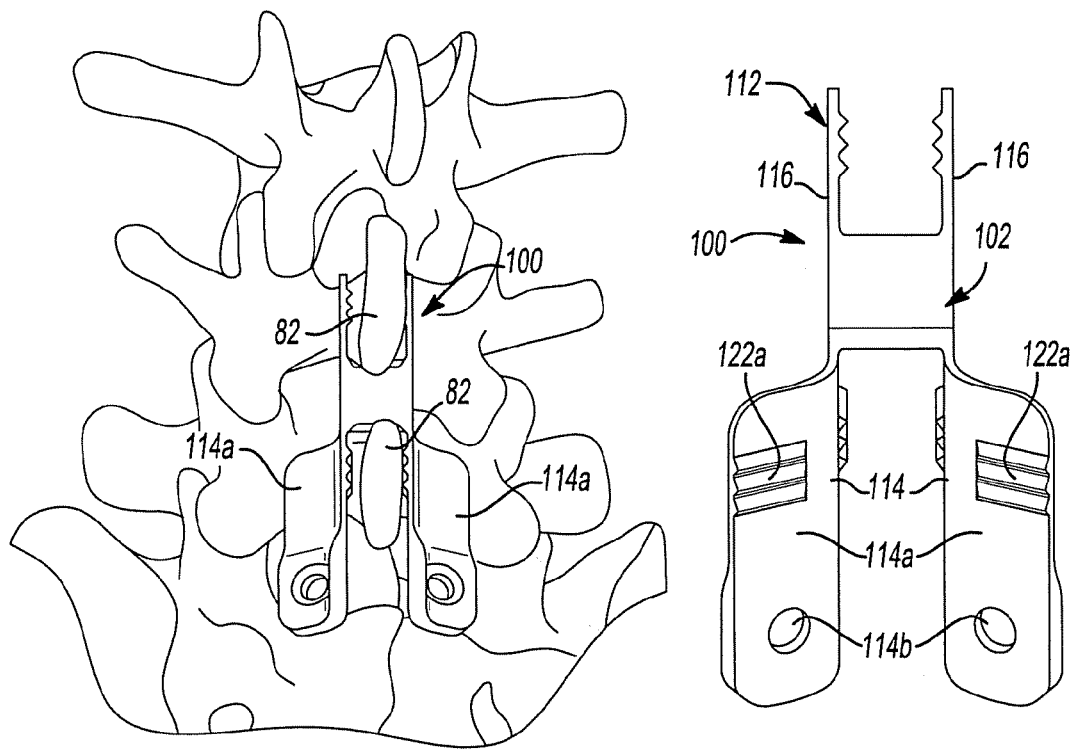
Fig-16A
Fig-16C
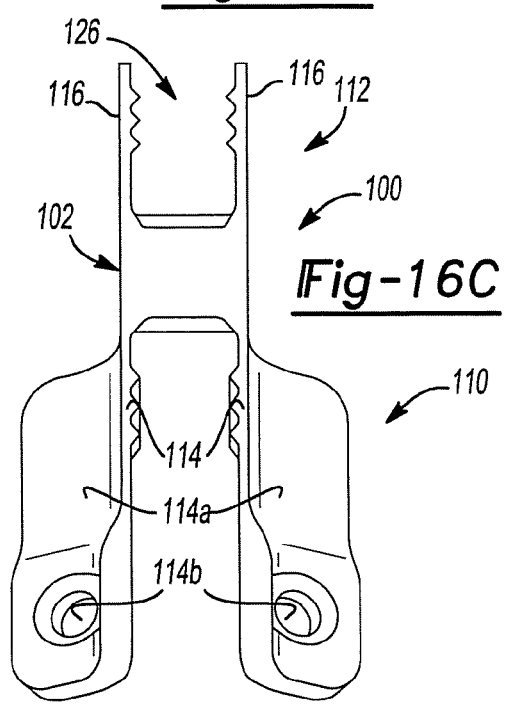
Fig-16B

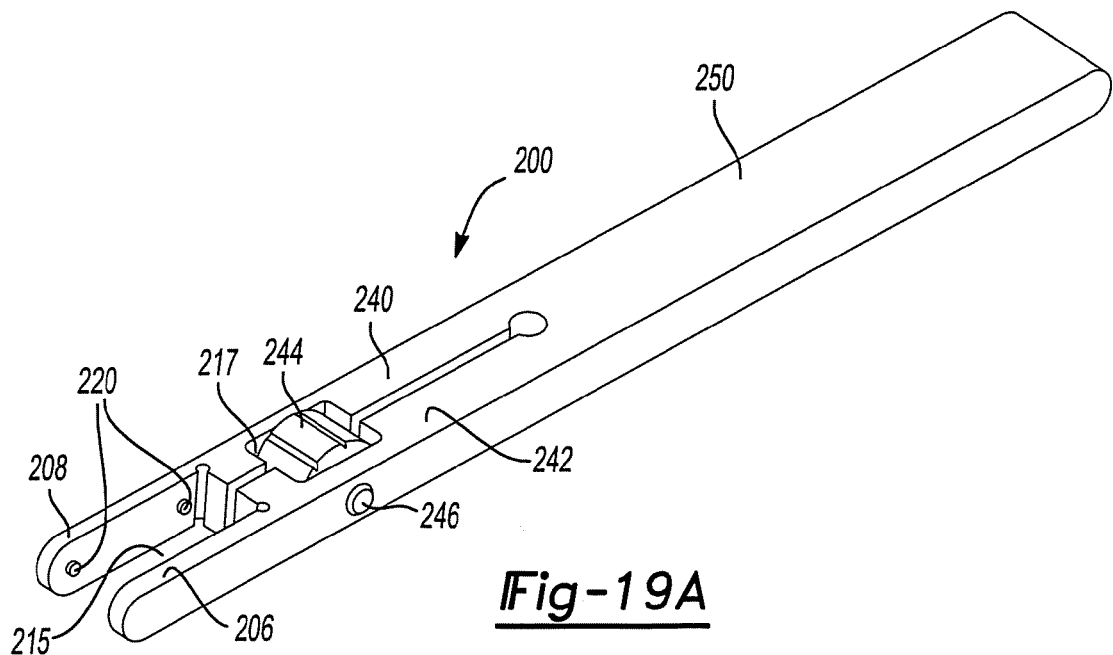
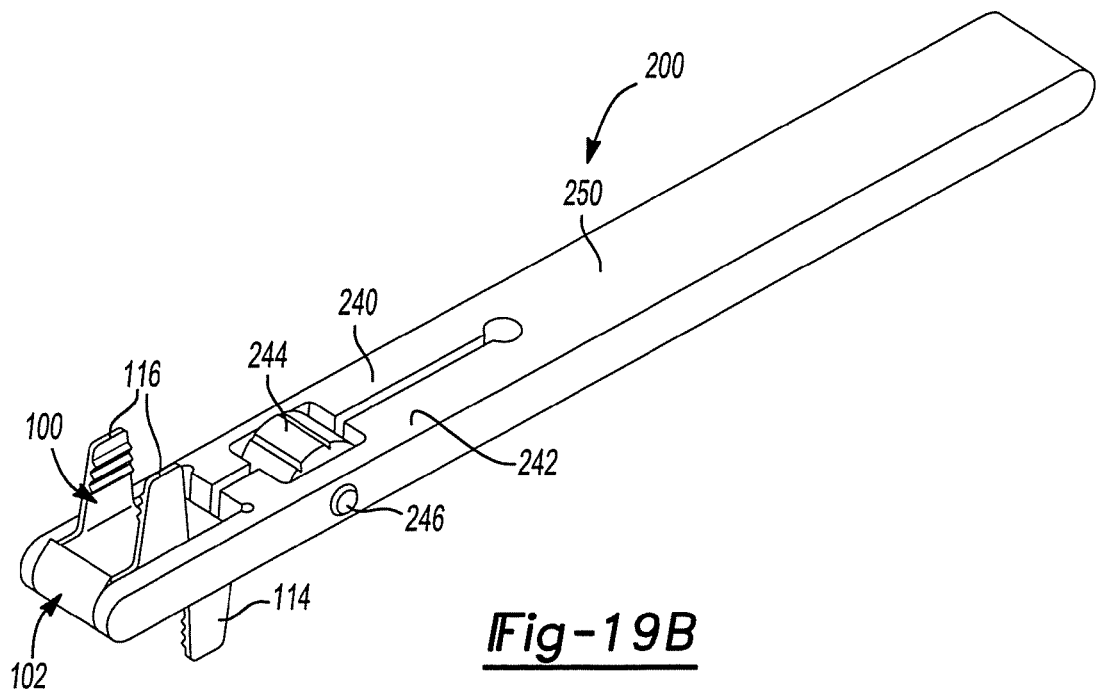

INTERSPINOUS IMPLANT

INTRODUCTION

Various interspinous implants are known for correcting damaged intervertebral disks or other conditions that can subject the spinous processes of adjacent vertebrae to stresses, overextension, painful wear and tear, or general instability of the spinal column.

The present teachings provide an interspinous implant that can stabilize the spine and limit overextension of the spine and excessive spacing between the superior and inferior processes.

SUMMARY

The present teachings provide an interspinous implant that includes a substantially S-shaped body having a longitudinal anterior-posterior axis and first and second ends, a first U-shaped extension attached to the first end, and a second U-shaped extension attached to the second end. The first and second extensions can be oriented at an angle relative to the anterior-posterior axis and engageable to first and second spinous processes. The second extension can be offset relative to the first extension along the anterior-posterior axis. In one aspect, the S-shaped body can be resilient and can include a first portion having first and second ends and being substantially U-shaped, a second portion having first and second ends and being substantially U-shaped, and an intermediate portion connecting the second end of the first portion and the first end of the second portion.

The present teachings also provide an interspinous implant that includes a resilient S-shaped body including first and second saddle-shaped portions, and first and second stirrup-shaped brackets extending at an angle and in opposite directions from the first and second saddle-shaped portions. The first and second stirrup-shaped brackets can engage first and second spinous processes.

Further areas of applicability of the present teachings will become apparent from the description provided hereinafter. It should be understood that the description and specific examples are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 3 is a side view of two interspinous implants according to the present teachings, the interspinous implants shown implanted in a spine;

FIG. 4 is a perspective view of an interspinous implant according to the present teachings;

FIG. 5 is a rear view of the interspinous implant of FIG. 4;

FIG. 8 is a perspective view of an interspinous implant according to the present teachings;

FIG. 9 is a side view of the interspinous implant of FIG. 8;

FIG. 10 is a rear view of the interspinous implant of FIG. 8;

FIG. 16 is an environmental view of an interspinous implant according to the present teachings, the interspinous implant shown implanted in a spine;

FIG. 16A is a rear view of the interspinous implant of FIG. 16;

FIG. 16B is a side view of the interspinous implant of FIG. 16;

FIG. 16C is a front view of the interspinous implant of FIG. 16;

FIG. 19A is a perspective view of an inserter for an interspinous implant according to the present teachings;

FIG. 19B is a perspective view of the inserter of FIG. 19A, the inserter shown holding the interspinous implant;

DESCRIPTION OF VARIOUS ASPECTS

The following description is merely exemplary in nature and is in no way intended to limit the present teachings, applications, or uses. The present teachings generally provide an interspinous implant that can be used to limit overextension of the spine and provide normal motion. Further, the interspinous implant can stabilize the posterior spinous processes and promote fusion of the vertebral bodies. The present teachings can be used to provide interspinous implants for procedures intended to alleviate conditions resulting from damaged intervertebral disks, spinal stenosis or other conditions that can subject the spinous processes of adjacent vertebrae to stresses, overextension, painful wear and tear, or general instability of the spinal column. According to the present teachings, the interspinous implant can be used at any level of the spine, including L5-S1 level.

Figure 1:
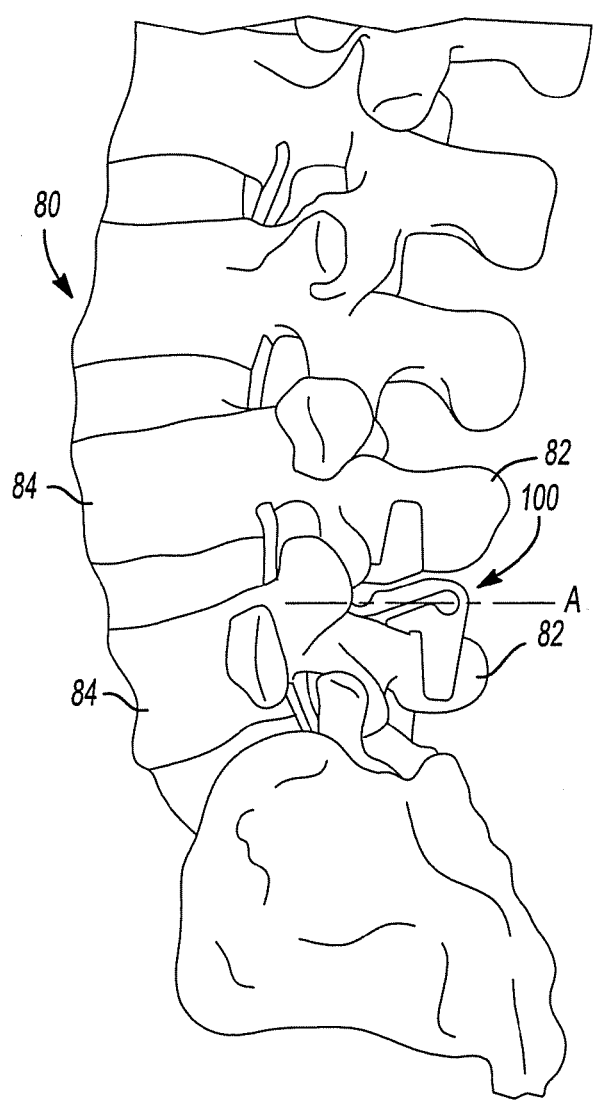
FIG. 1 is a side view of an interspinous implant according to the present teachings, the interspinous implant shown implanted in a spine.
Figure 2:
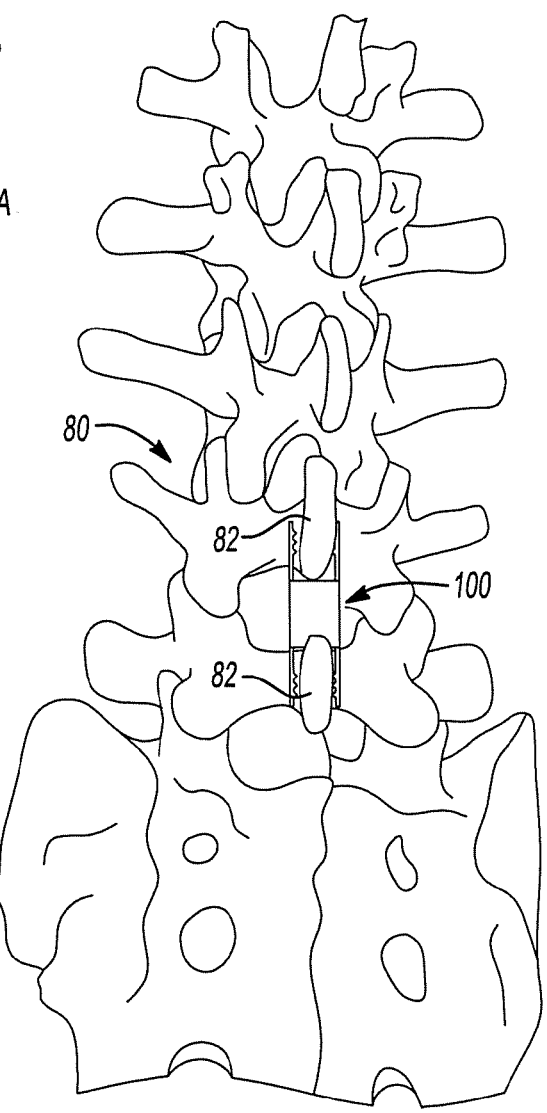
FIG. 2 is a rear view of the interspinous implant of FIG. 1, the interspinous implant shown implanted in a spine.

Referring to FIGS. 1 and 2, an exemplary interspinous implant 100 according to the present teachings is illustrated as implanted between two spinous processes 82 of adjacent or contiguous vertebrae 84 of a spine 80. It will be appreciated that one or more interspinous implants 100 can be used, as determined by the surgeon. Referring to FIG. 3, for example, two interspinous implants 100 are illustrated as implanted in a spine 80.

Referring to FIGS. 4-14C, and 16-17B, the interspinous implant 100 can include a body 102, and first and second extensions or brackets 112, 110. The body 102 can include first and second substantially U-shaped or saddle-shaped portions 104, 106 connected to one another by an intermediate portion 108. The first and second portions 104, 106 are oriented on opposite sides of the intermediate portion 108 along an axis A, in an opposing or antagonizing fashion, such that the body 102 can be substantially S-shaped. The body 102 can be made to be resilient such that the body 102 can operate as a tension spring or, as discussed below. Upon implantation, the axis A of the body 102 is oriented in the anterior-posterior direction, as shown in FIG. 1, such that spine loads can be distributed over both first and second U-shaped portions 104, 106, thereby reducing by about half the load carried by each portion 104, 106.

The first extension 112, or the second extensions 110, or both can be either fixedly or modularly connected to the body 102. The modular connection can be, for example, a taper connection, a dovetail connection, a snap fit connection, or other modular-type connection that allows easy removal of the corresponding first or second extension 112, 110 for minimally invasive insertion.

In another aspect, the first and second extensions 110, 112 can be movably connected to the body 102, such that the first and second extensions 110, 112 can be moved to a compact configuration for inserting the interspinous implant 100 into the spine. For example, the first and second extensions 110, 112 can be connected to the body 102 by pins received in corresponding elongated apertures or slots formed through the first and second extensions 112, 110. Translational movement of the first and second extensions 110, 112 relative to the body 102, with the pins sliding along the corresponding slots, can collapse the first and second extensions 110, 112 relative to the body 102 into a compact configuration. In another example, the first and second extensions 110, 112 can be rotatably coupled to the body 102, with hinges, for example. The first and second extensions 110, 112 can be rotated relative to the body 102 to a compact configuration for inserting the interspinous implant 100 into the spine.

In another aspect, one of the first or second extensions 112, 110 can be omitted. For example, the inferior extension 110 can be omitted and the body 102 can be formed as curved member that can act as an extension stop that does not limit flexion. Various fasteners, including screws, bolts, sutures or cables can pass through openings, such as holes or elongated slots or other apertures provided through the first and second extensions 122, 110 or the body 102, for securing the interspinous implant 100 to the spinous process 82.

Figure 6:
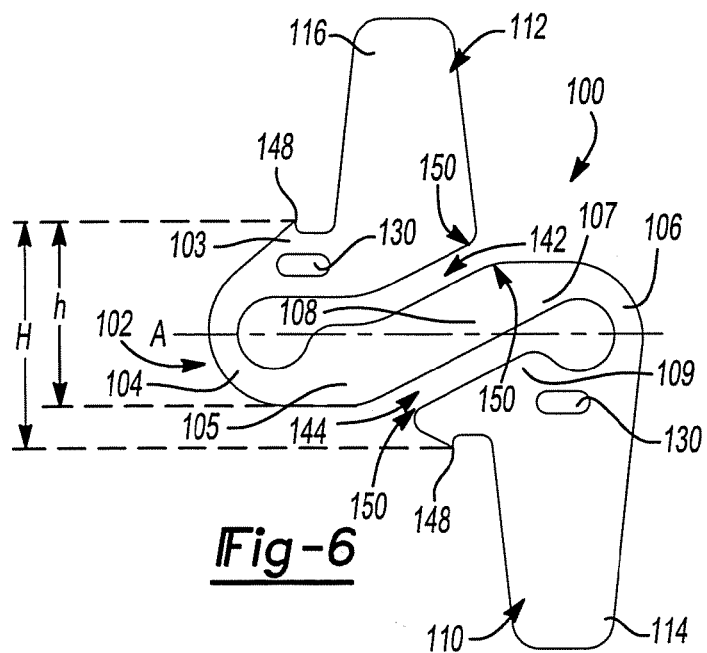
FIG. 6 is a side view of the interspinous implant of FIG. 4, shown in a first configuration.
Figure 6A:
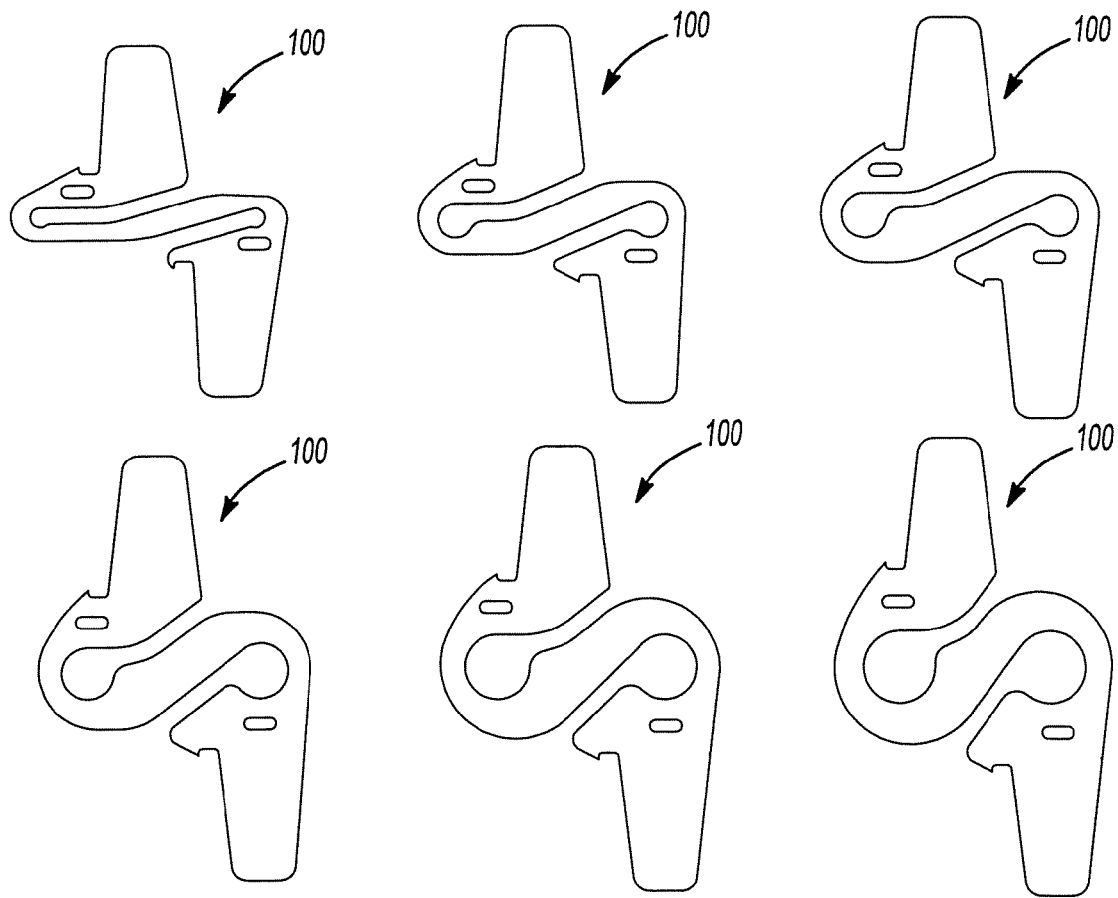
FIG. 6A illustrates side views of a series of representative interspinous implants according to the present teachings.

Referring to FIGS. 6 and 6A, exemplary sizes and shapes of the intervertebral implant 100 are illustrated. Referring to FIG. 6, for example, the first U-shaped portion 104 can include first and second ends 103, 105, and the second U-shaped portion 106 can include first and second ends 107, 109. The intermediate portion 108 can connect the second end 105 of the first portion 104 to the first end 107 of the second portion 106. The first and second extensions 112, 110 can extend substantially perpendicularly or at another angle relative to the axis A from the first and second ends 103, 109 of the first and second portions 104, 106 respectively.

The first and second extensions 112, 110 can be in the form of stirrup-shaped brackets for receiving corresponding adjacent spinous processes 82. The first extension 112 can include a pair of tabs or legs 116 defining an opening 126 for receiving a first spinous process 82. Each leg 116 can include anti-slip formations 122 for supporting, or engaging as needed, the spinous process 82. The anti-slip formations 122 can be in the form of series of sagittal teeth that may be interrupted by a coronal break 124 defining two columns 123, as illustrated in FIG. 4. Similarly, the second extension 110 can include a pair of tabs or legs 114 defining an opening 128 for receiving a second spinous process 82. Each leg 114 can include anti-slip formations 122 for supporting or engaging the spinous process 82. In one aspect, and in particular when the interspinous implant 100 is made of metal, such as titanium or other biocompatible metal, the first and second extensions 112, 110 can be crimped onto to the corresponding spinous processes 82 for engaging the spinous processes 82. The first and second extensions 112, 110 can also be fastened with screws or bolts or other fasteners on the spinous processes.

Figure 7:
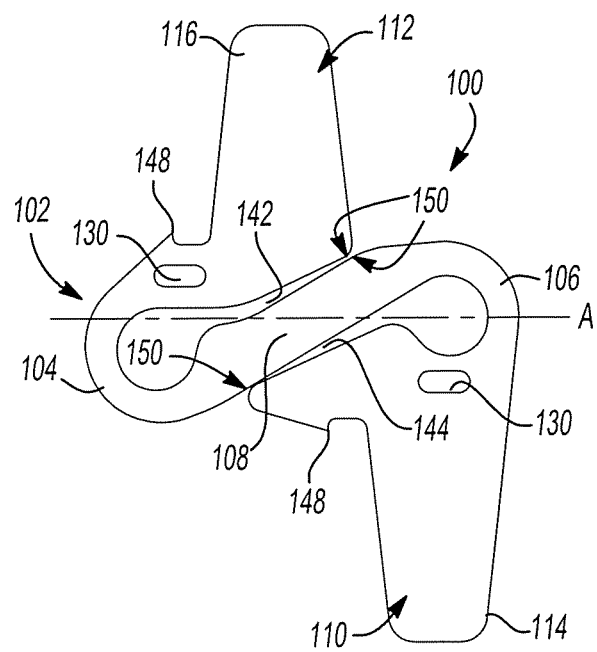
FIG. 7 is a side view of the interspinous implant of FIG. 4, shown in a second configuration.
Figure 7A:
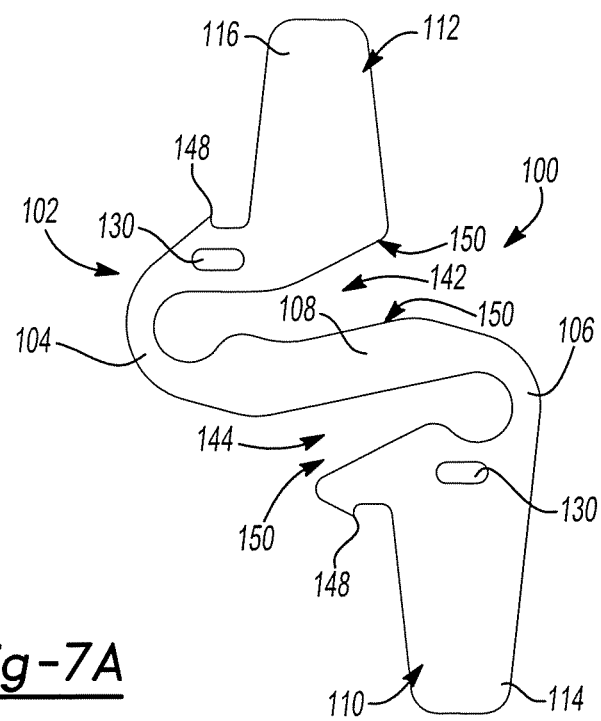
FIG. 7A is a side view of the interspinous implant of FIG. 4, shown in a second configuration.
Figure 11:
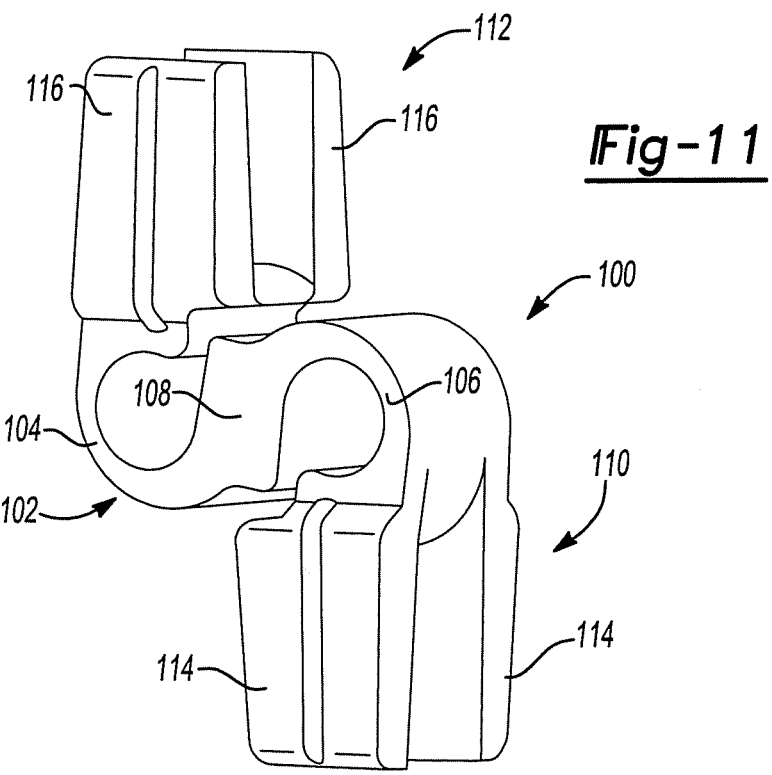
FIG. 11 is a perspective view of an interspinous implant according to the present teachings.
Figure 12:
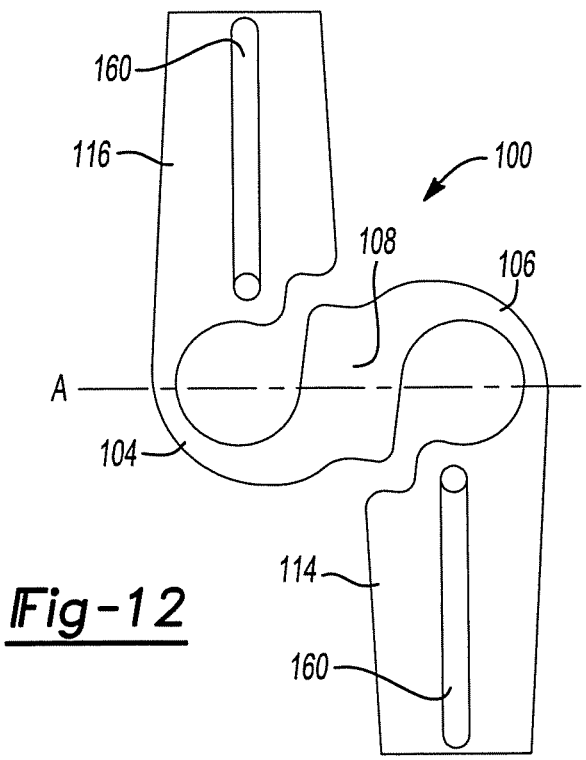
FIG. 12 is a side view of the interspinous implant of FIG. 11.

Referring to FIGS. 6, 7 and 7A, the geometry and construction of the body 102 can allow the body 102 to move between several configurations, including a first undeformed (or expanded) configuration, shown in FIG. 6, a second deformed and closed or collapsed configuration, shown in FIG. 7 and a third deformed and expanded configuration, shown in FIG. 7A. The first and second U-shaped portions 104, 106 can define corresponding first and second channels or gaps 142, 144 relative to the intermediate portion 108. In the undeformed configuration, the first and second channels 142, 144 can remain completely open with open end portions 150, as shown in FIG. 6, such that each channel 142, 144 forms an open loop. In the deformed and closed configuration, the end portions 150 of the first and second channels 142, 144 can close, as shown in FIG. 7, such that each channel 142, 144 forms a closed loop. In the deformed and open configuration the first and second channels 142, 144 can remain completely open and the end portions 150 can diverge further from the undeformed configuration, as shown in FIG. 7A. Accordingly, the end portions 150 can effectively define positive safety stops that prevent over-compression of the resilient body 102 and corresponding overextension of the spine 80 posteriorly, and also can limit fatigue loads and fatigue failure of the intervertebral implant 100.

The thickness or shape and size of the body 102 can be determined such that the body 102 only deforms elastically in a spring-like fashion and plastic deformation is avoided. For example, the intermediate portion 108 can have increased thickness relative to the first and second U-shaped portions 104, 106, and the body 102 can be shaped such that forces can be distributed through the thicker intermediate portion 108 or equally through the first and second portions 104, 106. Generally, the thickness and shape of the body 102 can vary, as shown in FIG. 6A, such that different motion characteristics can be provided. The force distributing and resiliency characteristics of the body 102 can allow use of biocompatible materials that have modulus more similar to bone than titanium and other metals, including, for example, PEEK, or other biocompatible polymeric materials in addition to metals.

Figure 13:
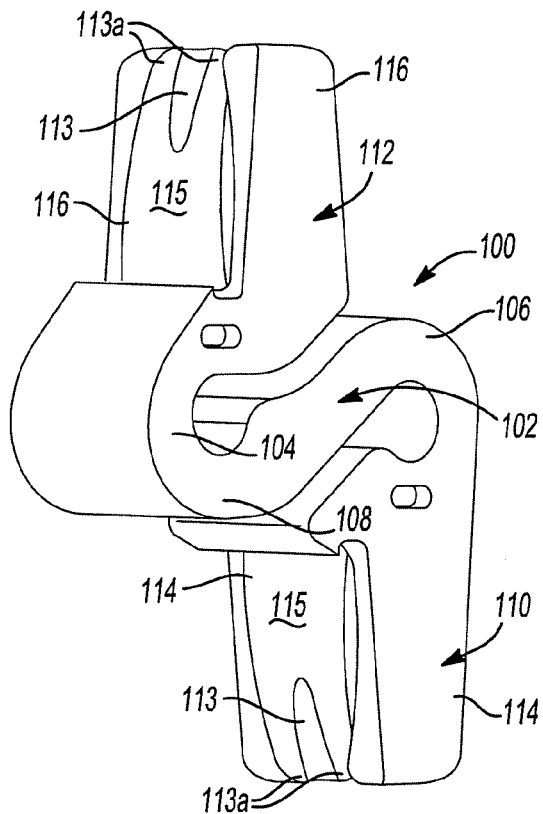
FIG. 13 is a perspective view of an interspinous implant according to the present teachings.
Figure 13A:
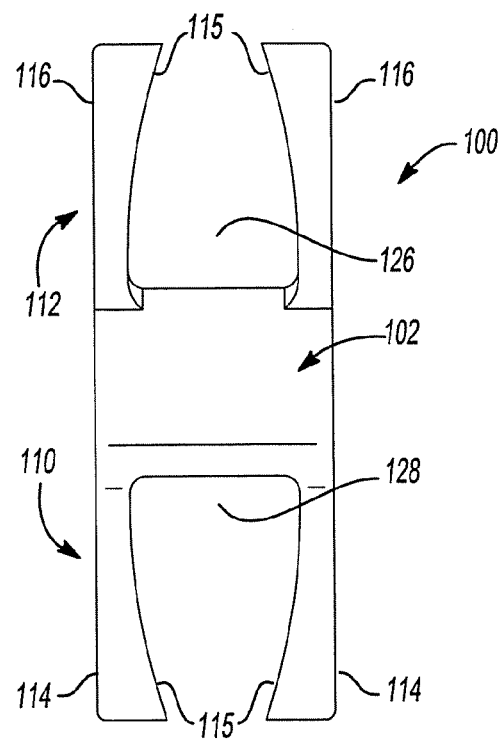
FIG. 13A is a rear view of the interspinous implant of FIG. 13.
Figure 13B:
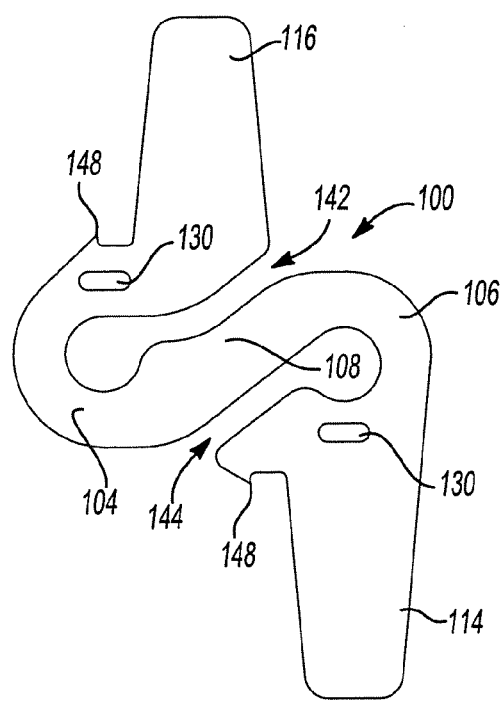
FIG. 13B is a side view of the interspinous implant of FIG. 13.

An exemplary interspinous implant 100 constructed from PEEK is illustrated in FIGS. 13, 13A and 13B. Instead of discrete anti-slip formations, the profile of the legs 116, 114 of the first and second extensions 112, 110 of the interspinous implant of FIG. 13 can be modified such that each leg 116, 114 can have a curved inner surface 115, and the corresponding leg 116, 114 has a thickness that increases away from the body 102. Each inner surface 115 can curve distally toward the curving surface 115 of the opposing leg 116, 114 of its corresponding extension 112, 110. Accordingly, the corresponding openings 126, 128 between the pair of legs 116, 114 can decrease away from the body 102, as shown in FIG. 13. In this manner, the first and second extensions 112, 110 can form scallop-like clips that can clamp onto the spinous processes 82 without crimping. The curved surfaces 115 can optionally include a relieved portion 113 defining teeth 113a for better fixation.

The body 102 can also include superior and inferior teeth or other superior and inferior engagement formations 148 for better fixation in the spine and resistance to expulsion, as shown in FIGS. 4 and 8, for example. In one aspect, the first U-shaped portion 104 of the body 102 can define an anterior surface 101 protruding into the vertebral foramen, such that the load on the disc space may be reduced, as shown in FIGS. 1 and 4.

Referring to FIGS. 8-10, each leg 116, 114 of the first and second extensions 112, 110 can have a U-shaped opening or channel 154 defining a cantilevered or overhanging flange 152 that can operate as a resilient spring or clip for engaging the spinous processes 82 and allowing passage of a cable, ligament, graft or suture. In another aspect, referring to FIGS. 11 and 12, each leg 116, 114 of the first and second extensions 112, 110 can include a longitudinal through-groove 160 substantially perpendicular or at another angle relative to the axis A of the body 102. The longitudinal groove 160 can provide an access space for a cable, suture or other graft and can also reduce the thickness of each leg 116, 114 and increase the resilience of the first and second extensions 112, 110.

Figure 14:
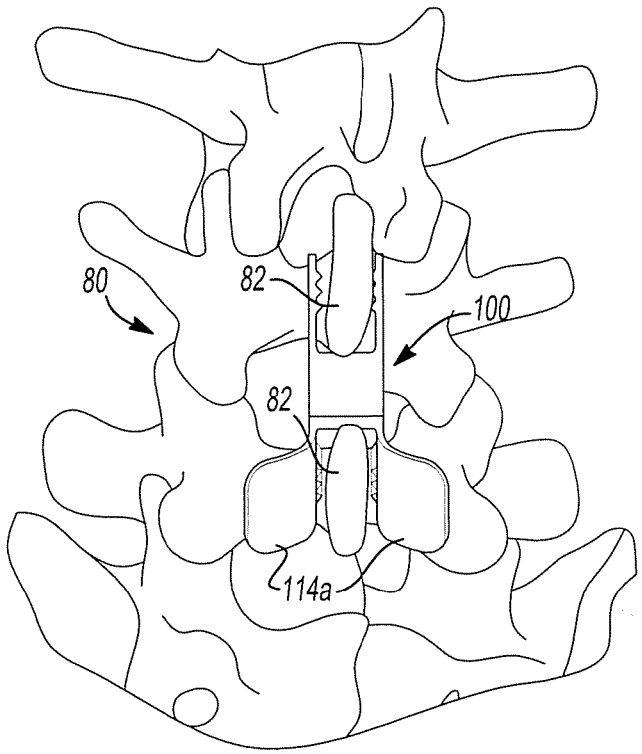
FIG. 14 is an environmental view of an interspinous implant according to the present teachings, the interspinous implant shown implanted in a spine.
Figure 14A:
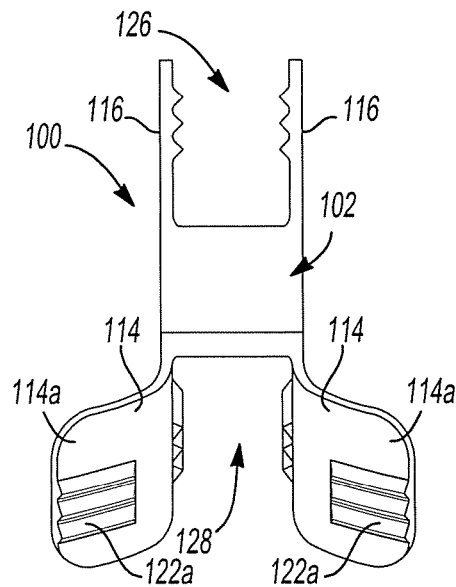
FIG. 14A is a rear view of the interspinous implant of FIG. 14.
Figure 14B:
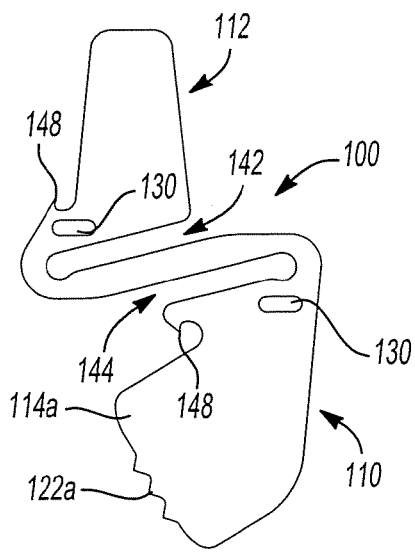
FIG. 14B is a side view of the interspinous implant of FIG. 14.
Figure 14C:
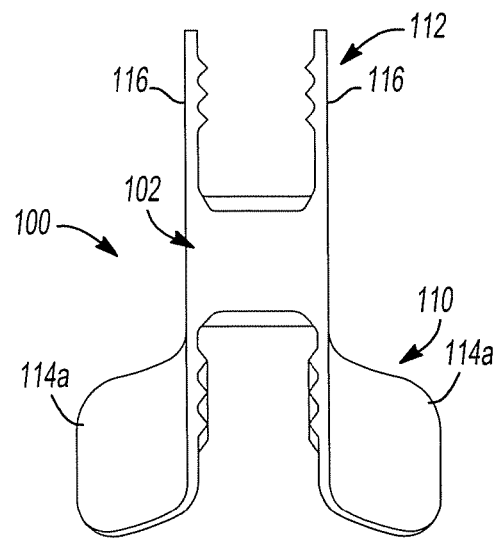
FIG. 14C is a front view of the interspinous implant of FIG. 14.
Figure 17A:
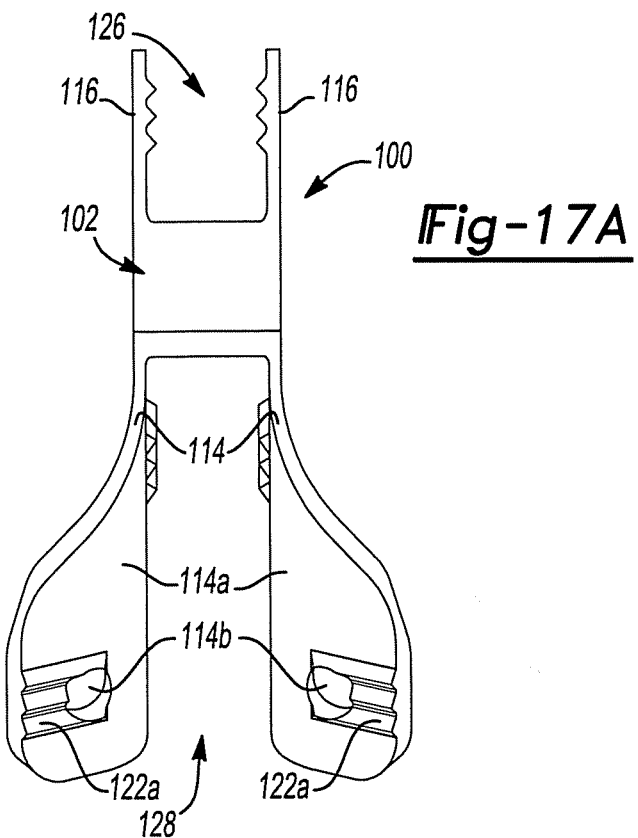
FIG. 17A is rear view of an interspinous implant according to the present teachings.
Figure 17B:
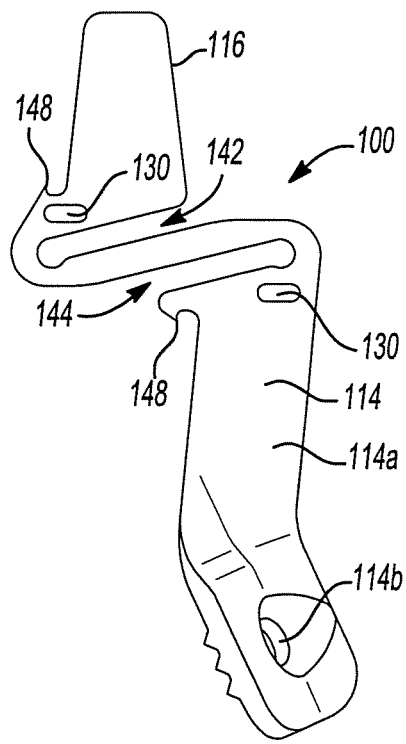
FIG. 17B is a side view of the interspinous implant of FIG. 17A.
Figure 17C:
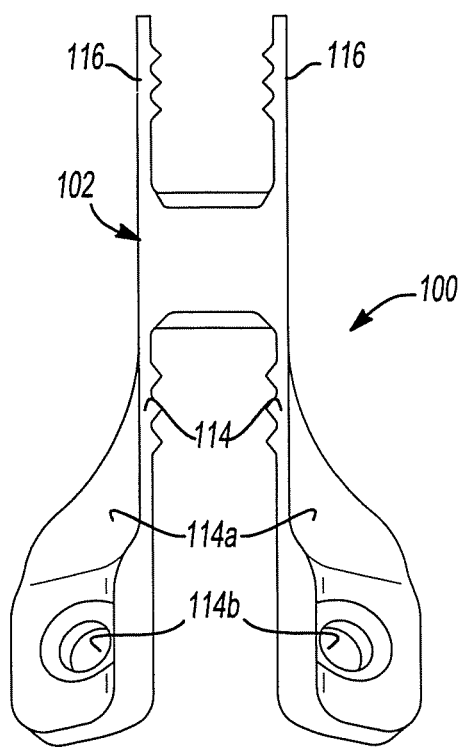
FIG. 17C is a front view of the interspinous implant of FIG. 17A.

Referring to FIGS. 14-14C, 16-16C, and 17A-17C, the legs 114 of the second extensions 110 can include extended wide flanges 114a that can engage the lamina of the corresponding vertebra 84. The flanges 114a can include teeth, serrations or other anti-slip formations 122a, as shown in FIGS. 14A, 16A and 17A, for example. In one aspect, the flanges 114a can include holes for receiving screws or other bone fasteners (not shown). It will be appreciated that the interspinous implant 100 can be used at any level of the spine, including the L5-S1 level.

Figure 15:
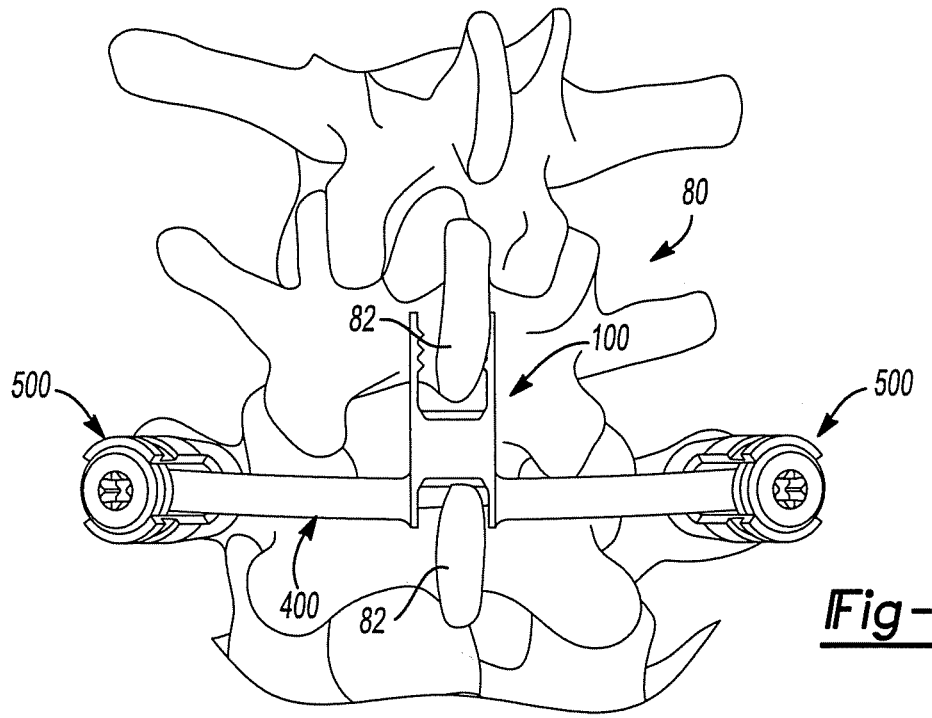
FIG. 15 is an environmental view of an interspinous implant according to the present teachings, the interspinous implant shown implanted in a spine.
Figure 15A:
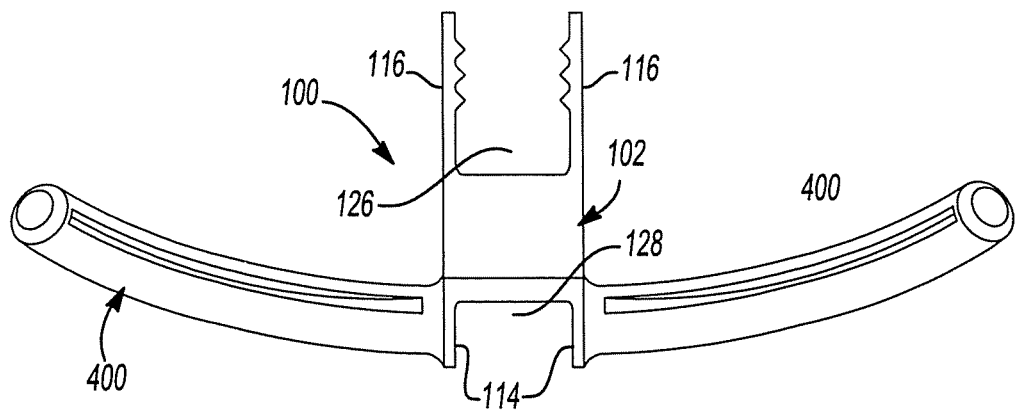
FIG. 15A is a rear view of the interspinous implant of FIG. 15.
Figure 15B:
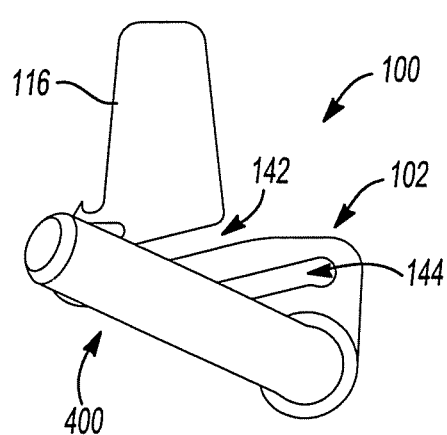
FIG. 15B is a side view of the interspinous implant of FIG. 15.

Referring to FIGS. 15, 15A, and 15B, the interspinous implant 100 can include a spinal connecting element portion 400. The connecting element portion 400 can extend at an angle outwardly from each of the legs 114 and can be secured to the spine 80 with pedicle screws 500. The connecting element portion 400 can be an integral or modular portion of the interspinous implant 100. The connecting element portion 400 can be curved to follow the anatomy of the spine 80.

Figure 18A:
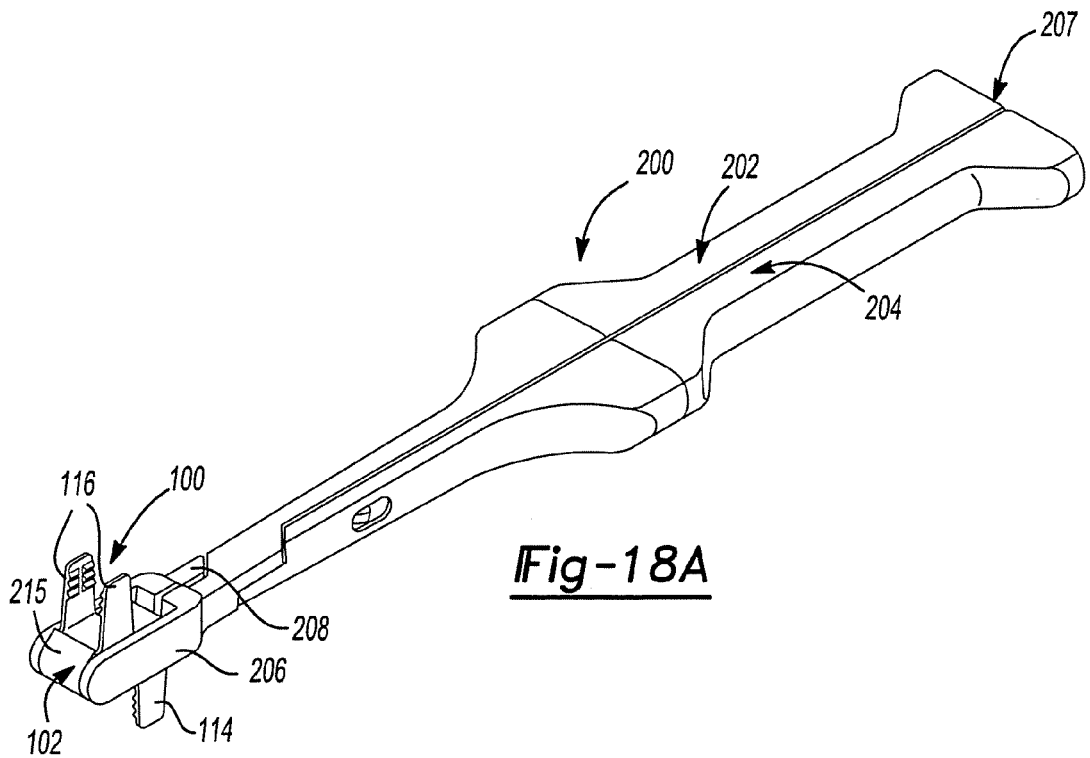
FIG. 18A is a perspective view of an inserter for an interspinous implant according to the present teachings, the inserter shown holding the interspinous implant.
Figure 18B:
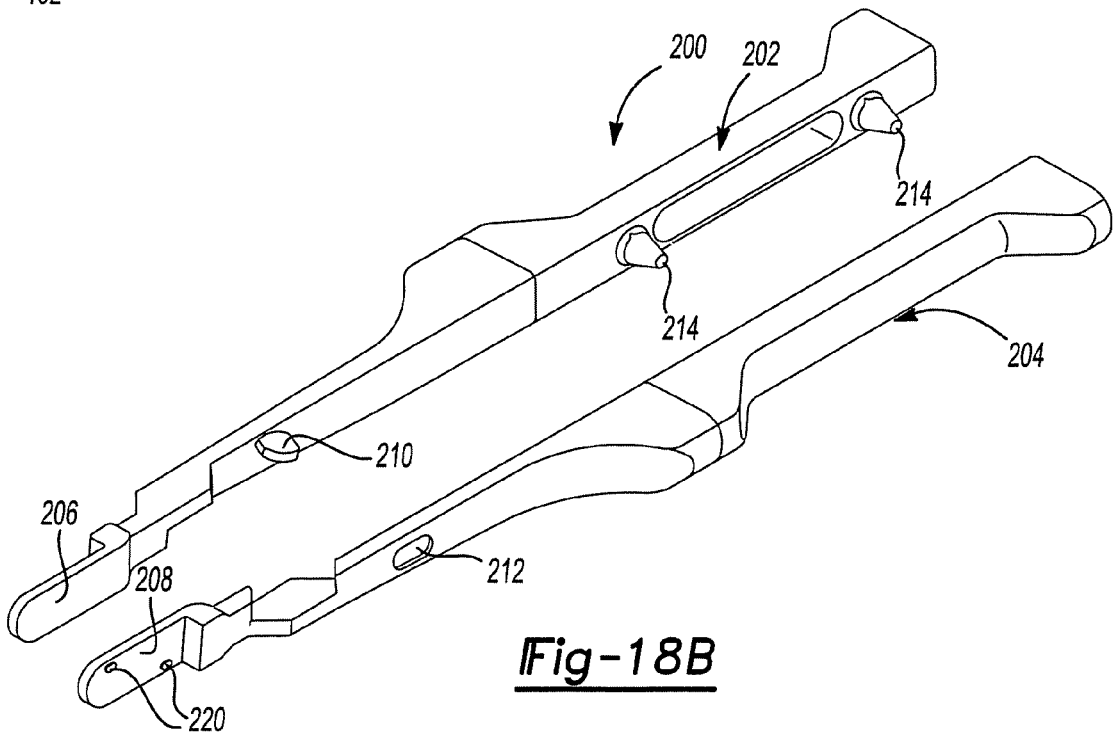
FIG. 18B is an exploded view of the inserter of FIG. 18A.
Figure 20A:
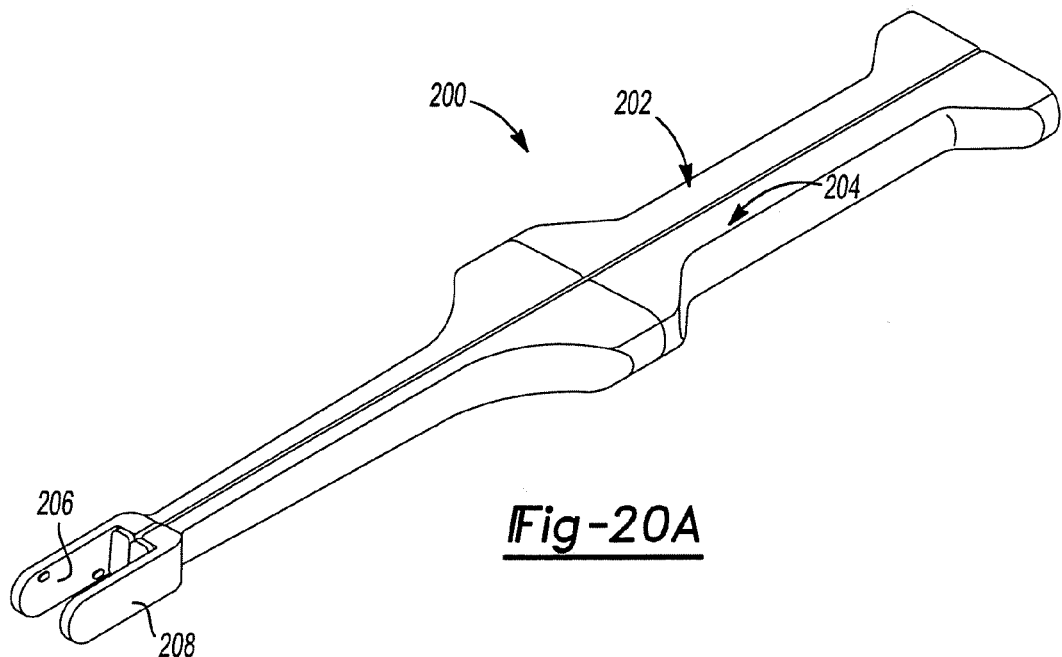
FIG. 20A is a perspective view of an inserter for an interspinous implant according to the present teachings.
Figure 20B:
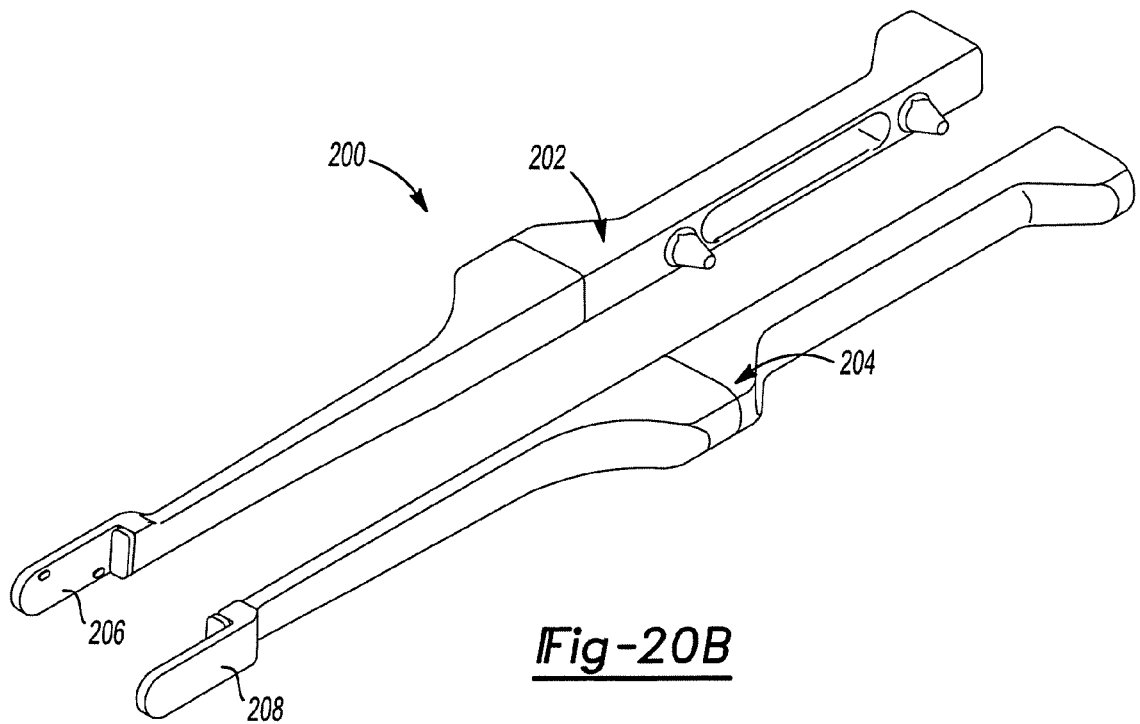
FIG. 20B is an exploded view of the inserter of FIG. 20A.

Referring to FIGS. 4, 13B, 14B, 16B, 17B, the body 102 can also include pairs of superior and inferior recesses 130 for engagement with an insertion/extraction tool 200, referenced as inserter 200 for short. The inserter 200 can be of a scissor-like type, as shown in FIGS. 18A and 18B, or of a tweezer-like type, as shown in FIGS. 19A and 10B, or chop-stick like type, as shown in FIGS. 20A and 20B. The insert 200 can be made of plastic or metallic materials and can provide cushioning for holding the interspinous implant 100. The inserter 200 can be size specific or universal.

Referring to FIGS. 18A and 18B, the scissor-like inserter 200 can include first and second handles 202, 204 that can be pivotably coupled and include a tongue 210 and an elongated slot 212 that can be engaged to prevent opening. The first and second handles 202, 204 can terminate in crossing and spaced-apart arms 206, 208. Each arm 206, 208 can include a pair of inward-facing protrusions 220 mateable for engagement with the corresponding pairs of recesses 130 of the interspinous implant 100. The spaced-apart arms 206, 208 can define an opening 215 sized to accommodate the size of the interspinous implant 100, as shown in FIG. 18A. The arms 206, 208 can be coated with appropriate materials to provide a better grip, while protecting the interspinous implant 100 from damage. Such materials can include, for example, nylon or polymeric materials that have modulus that is less than the modulus of the interspinous implant 100. At least a portion of the handles 202, 204 can be color coded to visually indicate a particular size of an interspinous implants 100. The handles 202, 204 can include pins or other features 214 for keeping the handles 202, 204 coupled to one another in a closed configuration. The end portions of the handles 202, 204 can define an enlarged surface 207 for attaching a striker plate (not shown) for facilitating insertion of the interspinous implant 100.

Referring to FIGS. 20A and 20B, the chop-stick like inserter 200 is similar to the scissor like inserter 200 shown in FIGS. 18A and 18B, except that the first and second handles 202, 204 are nor pivotably coupled and the arms 206, 208 do not cross each other.

Referring to FIGS. 19A and 19B, the tweezer-like inserter 200 can include a handle 250 bifurcating into first and second portions 240, 242 that define an opening for receiving a knob 244 rotatable about a pivot pin 246. The first and second portions 240, 242 can terminate in first and second parallel and spaced apart arms or jaws 208, 206. The arms 206, 208 can define an opening 215 for receiving the interspinous implant 100 and can include inner protrusions 220 for engaging the recesses 130 of the interspinous implant 100. Rotating the knob 244 in opposite directions can urge the arms 208, 206 to move between a first configuration for holding the interspinous implant 100, and a second configuration for releasing the interspinous implant 100. The handle 250 can be sized to operate as a trial sizer by matching certain dimensions of the body 102, such as width and height of the body 102. Optionally, the inserter 200 or a portion thereof can be color-coded to indicate implant size or match similarly color-coded interspinous implants 100.

Figure 21A:
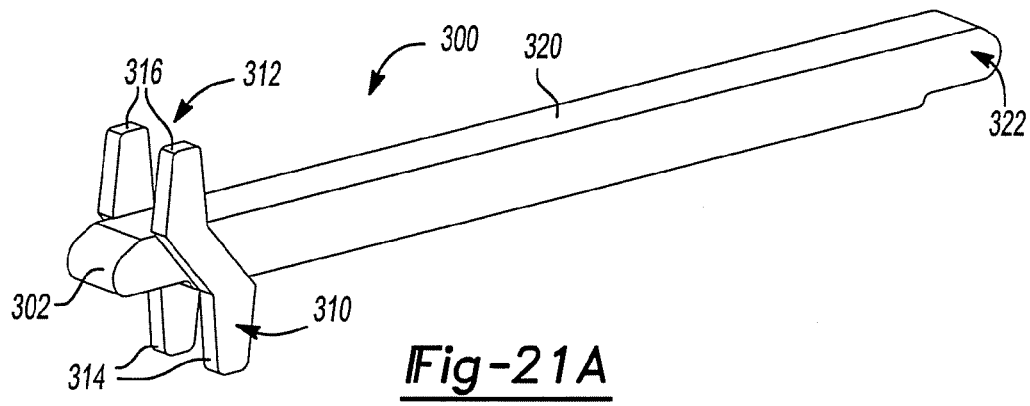
FIG. 21A is a perspective view of a trial sizer for an interspinous implant according to the present teachings.
Figure 21B:
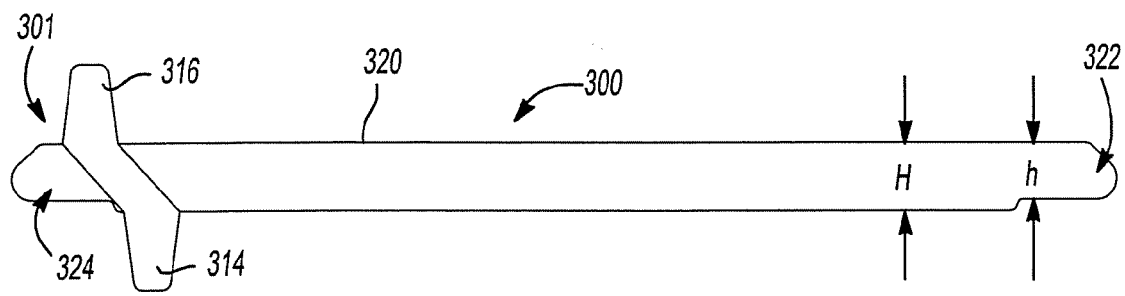
FIG. 21B is a side view of the trial sizer of FIG. 21A.
Figure 21C:
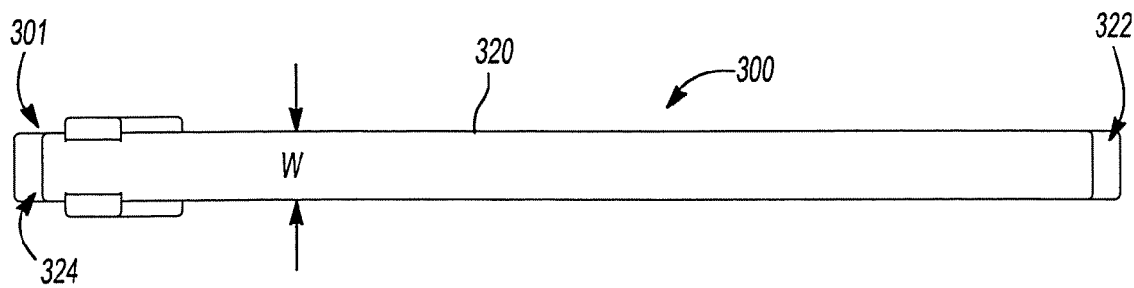
FIG. 21C is a plan view of the trial sizer of FIG. 21A.

Referring to FIGS. 21A-C, a trial sizer 300 can be used in association with the interspinous implant 100. The trial sizer 300 can include a shaft 320 having first and second ends 322, 324. The first end can have a height that matches the height the body 102 of the interspinous implant 100, as discussed below. The second end 324 can have a profile 301 that matches the entire anterior profile of the interspinous implant 100. The profile 301 can include an anterior surface 302 corresponding to the anterior surface of the body 102, and superior and inferior brackets 312, 310 with corresponding pairs of legs 316, 314 that match the profile of the first and second extensions 112, 110 of the interspinous implant 100. Referring to FIGS. 5, 6 and 21A-C, for example, the shaft 320 and the interspinous implant 100 can have matching width "W". Similarly, the heights "H" and "h" of the shaft 320 can match the total height "H" of the body 102 and the height "h" of the U-shaped (saddle) portions 104, 106 of the body.

The interspinous implant 100 can be inserted posteriorly through a minimal skin incision requiring little soft tissue dissection on either of the lateral sides of the spinous process 82 and lamina. The superspinous ligament may be preserved by clipping a small portion of the posterior process bone on the inferior surface of the superior process and the superior surface of the inferior process. A small portion of bone can remain attached to the ligament from both processes. Sufficient bone may be removed such that the ligament can be retracted slightly to one side allow the interspinous implant 100 to be inserted in a direct posterior fashion. After the interspinous implant 100 is inserted, the superspinous ligament can be replaced to fulfill its normal function. The clipped bone fragments (still attached to the ligament) can be reattached via a staple or suture. The bone can then be expected to fuse.

The interspinous implant 100 may also be inserted with complete bisection of the superspinous ligament at the affected level. After the interspinous implant 100 is inserted, the first and second extensions 112, 110 can be crimped down on the processes 82, fixing the interspinous implant 100 to the bone. Because the interspinous implant 100 can be rigidly attached to the superior and inferior spinous processes 82, the tension of the interspinous implant 100 can act as a mechanical replacement of the tension band supplied by the intact ligament. This function of the interspinous implant 100 can facilitate reducing loads in the disc space. The interspinous implant 100 can also be inserted laterally without modifying the spinous processes 82 or the superspinous ligament. The interspinous implant 100 can be inserted through the interspinous space, and then rotated within the sagittal plane into the appropriate position.

The foregoing discussion discloses and describes merely exemplary arrangements of the present teachings. One skilled in the art will readily recognize from such discussion, and from the accompanying drawings and claims, that various changes, modifications and variations can be made therein without departing from the spirit and scope of the teachings as defined in the following claims.

What is claimed is:

1. An interspinous implant comprising:
   a substantially S-shaped body having first and second ends;
   a first U-shaped extension attached to the first end, the first extension defining a first opening between a first pair of opposing legs and engageable to a first spinous process at the first opening;
   a second U-shaped extension attached to the second end, the second extension defining a second opening between a second pair of opposing legs and engageable to a second spinous process at the second opening;
   a first open saddle-shaped portion connected to the first U-shaped extension and having a first thickness;
   a second open saddle-shaped portion connected to the second U-shaped extension and having a second thickness; and
   an intermediate portion that is shared by the first and second saddle-shaped portions, the intermediate portion having a third thickness, the third thickness being greater than the first and second thicknesses;
   wherein the first and second open saddle-shaped portions are positioned on opposite sides of the intermediate portion in an opposing orientation along a body axis that crosses the first open saddle-shaped portion at the first thickness, the intermediate portion at the third thickness and the second open saddle-shaped portion at the second thickness and wherein the body axis is parallel to the first and second openings.

2. The implant of claim 1, wherein each leg of the first and second pairs of legs has an interior surface with a plurality of anti-slip formations.

3. The implant of claim 2, wherein each leg of the first and second pairs of legs has a cantilevered flange that is elongated in a direction perpendicular to the body axis.

4. The implant of claim 1, wherein the S-shaped body includes a pair of tool-engaging recesses.

5. The implant of claim 1, wherein the S-shaped body is resilient and defines safety stops preventing overextension.

6. The implant of claim 1, wherein the S-shaped body has an outer surface and includes anti-slip elements on inferior and superior portions of the outer surface.

7. The implant of claim 1, wherein the S-shaped body defines two channels that cross the body axis, the S-shaped body movable between a first configuration wherein end portions of the S-shaped body engage another portion of the S-shaped body such that at least one of the two channels forms a closed loop.

8. The implant of claim 1, wherein a leg of the first pair of legs extends longitudinally along a first leg axis and wherein a leg of the second pair of legs extends longitudinally along a second leg axis, wherein the first and second leg axes are parallel and offset relative to each other.

9. The implant of claim 8, wherein the first and second leg axes are both perpendicular relative to the body axis.

10. The implant of claim 1, wherein the S-shaped body has a body width defined perpendicularly to the body axis and wherein a leg of the first pair of legs has a leg width, wherein the body width and the leg width extend in directions that are perpendicular to each other.

11. An interspinous implant comprising:
    a resilient S-shaped body including first and second open saddle-shaped portions, the first open saddle-shaped portion having a first end, the second open saddle-shaped portion having a second end;
    an intermediate portion disposed between first and second open saddle-shaped portions and that connects the first and second open saddle-shaped portions, wherein the first and second open saddle-shaped portions are oriented on opposite sides of the intermediate portion along an axis that crosses the first and second open saddle-shaped portions at least two distinct locations;
    first and second stirrup-shaped brackets extending at an angle and in opposite directions from the first and second open saddle-shaped portions, the first and second stirrup-shaped brackets having respective openings that are both parallel to the axis and that are engageable to first and second spinous processes; and
    first and second connecting portions, the first connecting portion disposed between the first saddle-shaped portion and the intermediate portion, the second connecting portion disposed between the second saddle-shaped portion and the intermediate portion, the intermediate portion thicker than at least one of the first and second saddle-shaped portions,
    wherein the S-shaped body is configured to move between an expanded configuration and a closed configuration, wherein in the expanded configuration a first channel is defined between the intermediate portion and the first end and a second channel is defined between the intermediate portion and the second end, wherein in the closed configuration, at least one of the first end or the second end engages the intermediate portion.

12. The implant of claim 11, wherein the first stirrup-shaped bracket has a first pair of opposing legs, wherein the opening of the first stirrup-shaped bracket extends between the first pair of opposing legs.

13. The implant of claim 12, wherein the second stirrup-shaped bracket has a second pair of opposing legs, wherein the opening of the second stirrup-shaped bracket extends between the second pair of opposing legs.

14. The implant of claim 11, wherein the first and second stirrup-shaped brackets include first and second pairs of legs, respectively, a leg of the first pair of legs extends longitudinally along a first leg axis and wherein a leg of the second pair of legs extends longitudinally along a second leg axis, wherein the first and second leg axes are parallel and offset.

15. The implant of claim 11, wherein at least one of the first and second stirrup-shaped brackets includes a first pair of legs, the S-shaped body has a body width defined perpendicular to the axis and wherein a leg of the first pair of legs has a leg width, wherein the body width and the leg width extend in directions that are perpendicular to each other.

16. An interspinous implant comprising:
a resilient body having a longitudinal axis and a substantially S-shape, the resilient body comprising:
a first portion having first and second ends, the first portion being substantially U-shaped and having a first thickness;
a second portion having first and second ends, the second portion being substantially U-shaped and having a second thickness; and
an intermediate portion that is oriented between and that connects the second end of the first portion and the first end of the second portion, the intermediate portion having a third thickness that is greater than at least one of the first and second thicknesses, wherein the longitudinal axis crosses the intermediate portion at a location between the first and second portions;
a first extension attached to the first end of the first portion, the first extension having a first pair of elongated legs that are laterally spaced and extend perpendicular to the longitudinal axis and engageable to a first spinous process; and
a second extension attached to the second end of the second portion, the second extension having a second pair of elongated legs that are laterally spaced and extend perpendicular to the longitudinal axis and engageable to a second spinous process, the second extension offset relative to the first extension along the longitudinal axis.

17. The implant of claim 16, wherein the resilient body has an outer surface and includes anti-slip elements on inferior and superior portions of the outer surface on opposite sides of the longitudinal axis.

18. The implant of claim 16, wherein the resilient body defines two channels, the resilient body movable between a first configuration in which each channel forms an open loop and a second configuration in which end portions of the resilient body engage such that at least one of the two channels forms a closed loop.

* * * * *